US006712808B2

(12) United States Patent
Fujieda

(10) Patent No.: US 6,712,808 B2
(45) Date of Patent: Mar. 30, 2004

(54) LASER SURGERY APPARATUS

(75) Inventor: Masanao Fujieda, Toyohashi (JP)

(73) Assignee: Nidek Co., Ltd. (JP)

(*) Notice: Subject to any disclaimer, the term of this patent is extended or adjusted under 35 U.S.C. 154(b) by 0 days.

(21) Appl. No.: 09/964,448

(22) Filed: Sep. 28, 2001

(65) Prior Publication Data

US 2002/0040218 A1 Apr. 4, 2002

(30) Foreign Application Priority Data

Oct. 2, 2000 (JP) ....................................... 2000-306620

(51) Int. Cl.[7] ................................................ A61B 18/18

(52) U.S. Cl. ................................ 606/4; 606/5; 606/10; 606/12; 351/208; 351/209; 351/211

(58) Field of Search ........................... 606/4, 5, 10–12; 128/898; 351/208, 209, 211, 212

(56) References Cited

U.S. PATENT DOCUMENTS

| | | | | | |
|---|---|---|---|---|---|
| 5,425,727 | A | * | 6/1995 | Koziol | 606/5 |
| 5,442,412 | A | | 8/1995 | Frey et al. | 351/223 |
| 5,507,799 | A | | 4/1996 | Sumiya | |
| 5,556,395 | A | | 9/1996 | Shimmick et al. | |
| 5,562,656 | A | | 10/1996 | Sumiya | |
| 5,637,109 | A | * | 6/1997 | Sumiya et al. | 606/5 |
| 5,713,892 | A | | 2/1998 | Shimmick | |
| 5,800,424 | A | | 9/1998 | Sumiya | |
| 5,947,955 | A | | 9/1999 | Kadambi et al. | 606/4 |
| 6,004,313 | A | | 12/1999 | Shimmick et al. | 606/5 |
| 6,030,376 | A | * | 2/2000 | Arashima et al. | 606/4 |
| 6,203,539 | B1 | | 3/2001 | Shimmick et al. | |
| 6,245,058 | B1 | * | 6/2001 | Suzuki | 606/2 |
| 6,257,722 | B1 | * | 7/2001 | Toh | 351/208 |

FOREIGN PATENT DOCUMENTS

| | | |
|---|---|---|
| DE | 196 35 998 | 4/1998 |
| JP | 08-206074 | 8/1996 |
| JP | 11-113852 | 4/1999 |

* cited by examiner

*Primary Examiner*—Michael Peffley
*Assistant Examiner*—A Farah
(74) *Attorney, Agent, or Firm*—Rader, Fishman & Grauer PLLC

(57) ABSTRACT

A laser surgery apparatus is provided to minimize a burden on a patient and to obtain a good result of a surgical operation. The laser surgery apparatus for performing surgery on a patient's eye by irradiating a laser beam thereonto comprises an irradiation device provided with an irradiation optical system for irradiating the laser beam onto the patient's eye, a control device for controlling the irradiation device, and an informing device for informing the patient of at least either a first period of a laser irradiation period or a second period of the laser irradiation period or both.

16 Claims, 6 Drawing Sheets

LASER SURGERY APPARATUS

BACKGROUND OF THE INVENTION

1. Field of the Invention

The present invention relates to a laser surgery apparatus for performing surgery on a patient's eye by irradiating a laser beam thereonto.

2. Description of Related Art

For a laser surgery apparatus for performing surgery on a patient's eye by irradiating a laser beam thereonto, for example, a corneal surgery (keratorefractive surgery) apparatus which employs an excimer laser beam has been known. This kind of apparatus is used to correct a refractive error by irradiating an excimer laser beam onto a corneal surface for ablation of the corneal surface so as to alter a corneal curvature or to remove an affected part in the cornea. This type of apparatus requires the patient's eye to be stabilized (fixed) by having the eye fixed on a fixation target for irradiating a laser beam onto a desired position of the patient's eye. However, irradiation of a laser beam by using this kind of apparatus takes one minute or so at the most. The patient's eye has to be constantly fixed from beginning to end during laser irradiation, and the tension of the patient resulting from the eye fixation puts a serious burden on him/her.

SUMMARY OF THE INVENTION

The present invention has been made in view of the above circumstances and has an object to overcome the above problems and to provide a laser surgery apparatus with which a burden on a patient is expected to be minimized, and a good result of a surgical operation is expected to be obtained.

To achieve the objects and in accordance with the purpose of the present invention, as embodied and broadly described herein, a laser surgery apparatus for performing surgery on a patient's eye by irradiating a laser beam thereonto comprises irradiation means provided with an irradiation optical system for irradiating the laser beam onto the patient's eye, control means for controlling the irradiation means, and informing means for informing the patient of at least either a first period of a laser irradiation period or a second period of the laser irradiation period or both.

In another aspect of the present invention, a laser surgery apparatus for correcting a refractive error of a patient's eye by ablating its corneal tissue with a laser beam comprises an ablation unit which includes a laser light source emitting the laser beam and an irradiation optical system provided with an aperture of which opening region is changeable and with a projecting lens which projects the aperture on a cornea of the patient's eye, an informing unit which informs the patient of at least either a first period of a laser irradiation period or a second period of the laser irradiation period or both, and a control unit which controls the informing unit in accordance with a change of the opening region of the aperture.

Yet, in another aspect of the present invention, a laser surgery apparatus for operating on a patient's eye by irradiating a laser beam thereonto comprises an irradiation unit which includes a laser light source emitting the laser beam and an irradiation optical system irradiating the emitted laser beam onto the patient's eye, an eye fixation target presenting unit which presents a fixation target for the patient's eye fixation, and a control unit which controls the eye fixation target presenting unit to inform the patient of at least either a first period of a laser irradiation period or a second period of the laser irradiation period or both.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
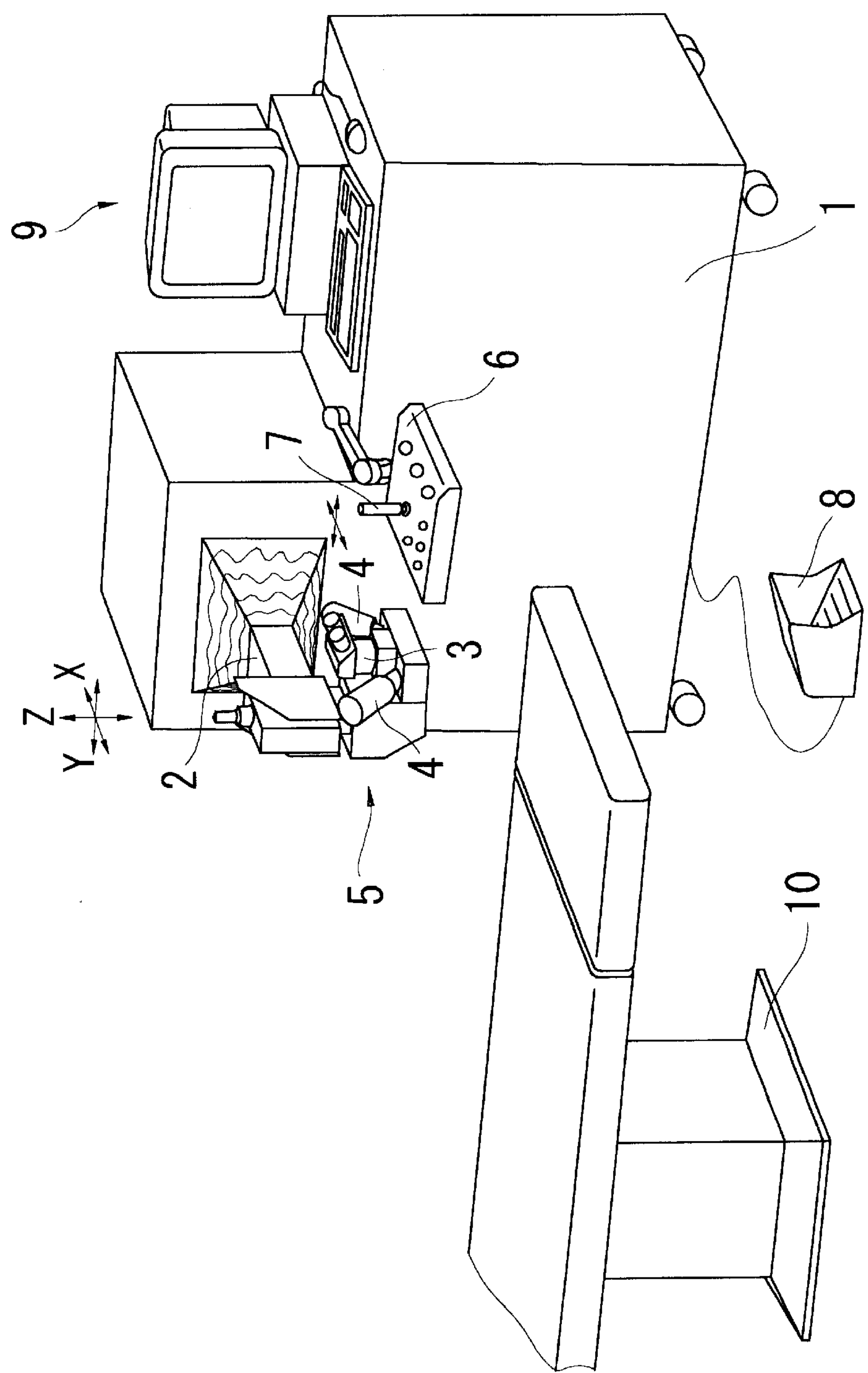
FIG. 1 is an external view of a corneal surgery apparatus consistent with a preferred embodiment of the present invention.
Figure 2:
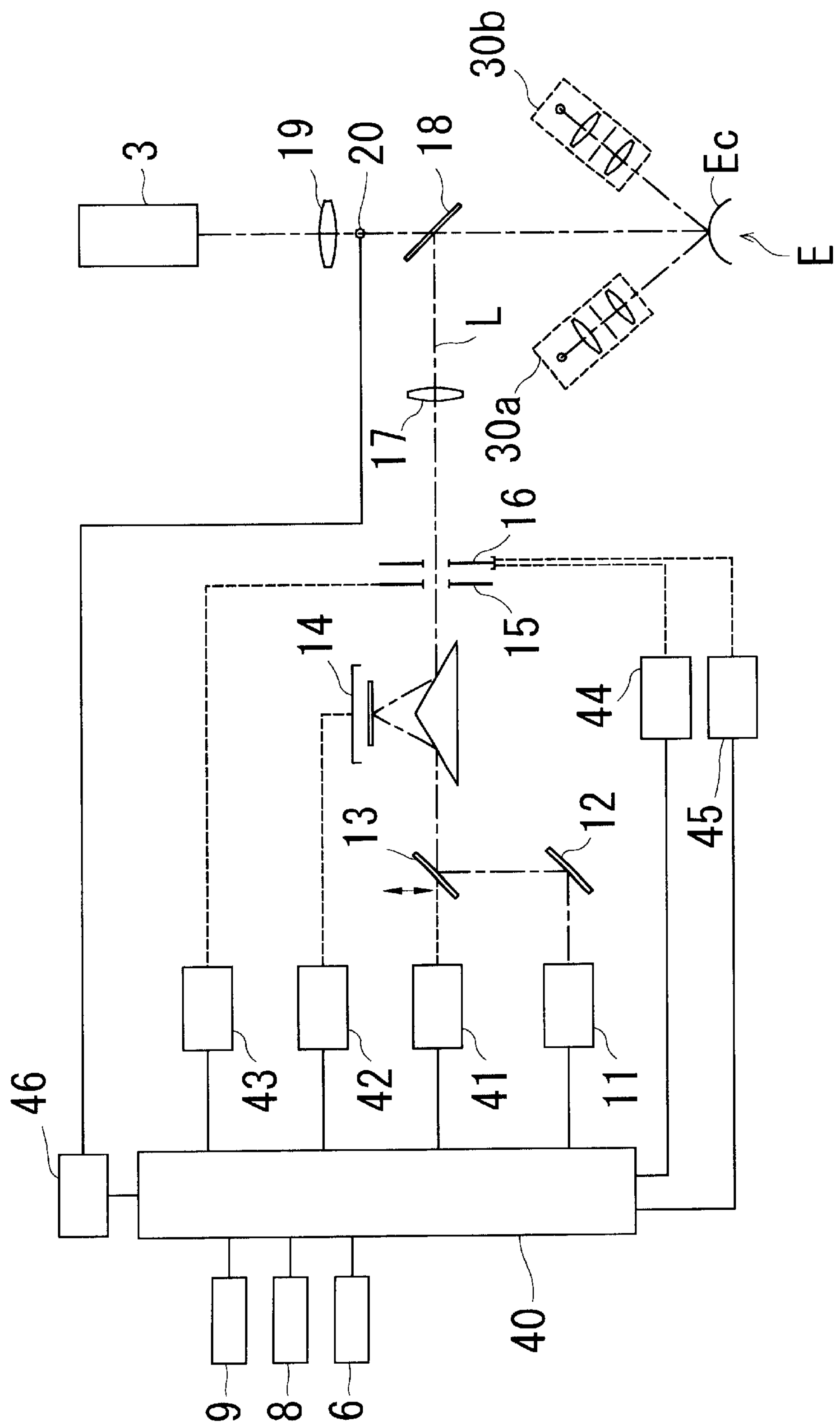
FIG. 2 is a view showing a schematic configuration of an optical system and a control system of the present apparatus.

A detailed description of one preferred embodiment of a laser surgery apparatus embodying the present invention will now be given referring to the accompanying drawings. FIG. 1 is an external view of a corneal surgery apparatus which is a type of laser surgery apparatus. FIG. 2 is a view showing a schematic configuration of an optical system and a control system of the present apparatus.

A main body 1 of the apparatus includes an excimer laser light source 11 therein. A laser beam from the laser light source 11 is reflected by a mirror provided in the main body 1 to be guided to an arm unit 2. An observation optical unit 5 is provided at an end portion of the arm unit 2. The observation optical unit 5 is provided with a binocular microscope unit 3 for observing a patient's eye E, an illumination unit 4, a laser irradiation exit, an eye-ball position detecting optical system, which are not illustrated, and so on. Also, the arm unit 2 is arranged to be movable in X- and Y-directions, and the observation optical unit 5 is arranged to be movable in a Z-direction. Each is configured to be moved by a driving unit which is not illustrated.

A controller 6 is provided with a joystick 7 for giving a signal to move the arm unit 2 in the X- and Y-directions, a switch for giving a signal to move the observation optical unit 5 in the Z-direction, and so on. A foot switch 8 is provided to give a signal for commencing laser irradiation (emission). A computer 9 is provided to compute ablation data by inputting various data on conditions for a surgical operation. Reference numeral 10 is a bed for a patient.

The laser light source 11 emits an excimer laser beam with a wavelength of 193 nm (not limited to this wavelength).

Figure 6:
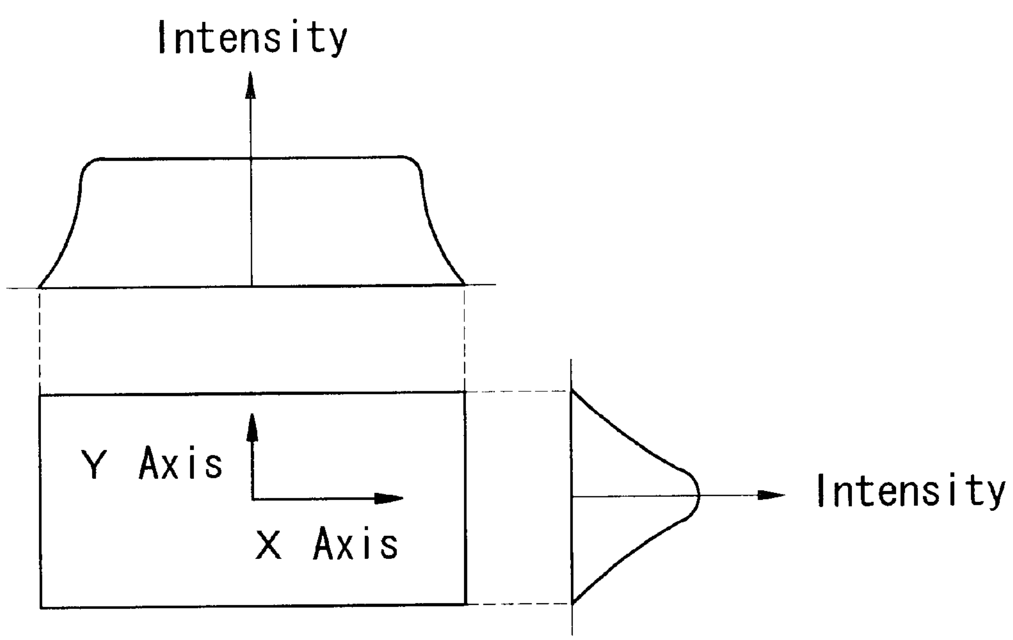
FIG. 6 is a graph showing an intensity distribution of an excimer laser beam.

The excimer laser beam emitted from the laser light source 11 is a pulse beam. Further, a cross-sectional shape of the pulse beam at a plane orthogonal to an optical axis of the laser beam is a narrow rectangle which is a typical shape. Also, an intensity distribution of the beam shows an approximately uniform distribution in a long-side direction of the rectangle, and it shows the Gaussian distribution in a short-side direction (see FIG. 6).

The laser beam emitted from the laser light source 11 is deflected 90 degrees by a plane mirror 12, and then it is further deflected 90 degrees by a plane mirror 13. The mirror 13 may be made in a direction of the arrow illustrated in the figure by a driving device 41 to have the laser beam make a parallel movement in the direction of the Gaussian distribution for ablating an object evenly.

An image rotator 14 is rotatably driven about an optical axis L by a driving device 42 to rotate the laser beam around the optical axis L. A changeable circular aperture 15 limits an ablation zone, and the region (diameter) of its opening is changed by a driving device 43. A changeable slit aperture 16 limits the ablation zone, and the region (width) of its opening is changed by a driving device 44. Also, the slit aperture 16 is rotated about the optical axis L by a driving device 45 so that the direction of the opening of the slit aperture is changed. This slit aperture 16 is used for astigmatic correction and the like.

A projecting lens 17 projects the circular aperture 15 or the slit aperture 16 on a cornea Ec of the eye E (the images of the circular aperture 15 and the slit aperture 16 are formed on the cornea Ec by the lens 17). A dichroic mirror 18 has a property which reflects the excimer laser beam and transmits visible light. The laser beam having passed through the lens 17 is reflected by the dichroic mirror 18 to be led to the cornea Ec.

The binocular microscope unit 3 is provided above the dichroic mirror 18 for observing an image of the anterior part of the eye E.

A fixation light 20 is disposed on an optical axis of an objective lens 19. It is arranged that illumination status of the fixation light 20 should be changed from staying lighted to flashing by a light control unit 46 when specified conditions are satisfied at the time of laser beam irradiation. It is preferable that a narrow bundle of light beams such as laser beams be used in order to minimize an influence by a change in visibility resulting from the keratorefractive surgery. In such a manner, a diameter of the light beam at the fundus becomes small when the patient fixes his/her eye on the fixation light 20, and the position of eye fixation is not extended.

Below the dichroic mirror 18, slit projecting optical systems 30*a* and 30*b* for alignment are provided in the illumination unit 4, and they are disposed at positions diametrically opposed to each other with respect to the optical axis of the lens 19 therebetween. The slit projecting optical systems 30*a* and 30*b* are constituted of a lamp, a condenser lens, a cross slit, a projecting lens, and the like. Further, a control unit 40 controls each unit.

A description of operations of the apparatus having the configuration mentioned above will be provided. In the present embodiment, its operation for correcting myopic astigmatism will be described.

An operator uses the computer 9 to input data on a refractive power of the eye E and data on refractive error correction including conditions for a surgical operation. Control data on corneal ablation are computed in the main body of the computer 9, and they are inputted into the control unit 40. After completing preparation for the surgical operation, the patient's eye E is fixed on the fixation light 20. While the operator observes an image of the slit projected on the cornea Ec by the projecting optical systems 30*a* and 30*b*, he/she performs alignment of the eye E by using the controller 6. After completing the alignment, the operator manipulates the foot switch 8 to emit the laser beam.

The control unit 40 makes the laser light source 11 emit the excimer laser beam when the foot switch 8 is operated. At the same time, the control unit 40 operates each driving device for irradiating the laser beam in accordance with the control data on corneal ablation computed by using the computer 9.

In the keratorefractive surgery (a surgical operation for correcting myopic astigmatism) consistent with the present embodiment, laser irradiation for astigmatic correction is carried out first, and laser irradiation for myopic correction is carried out next.

Astigmatic Correction

Figure 3:
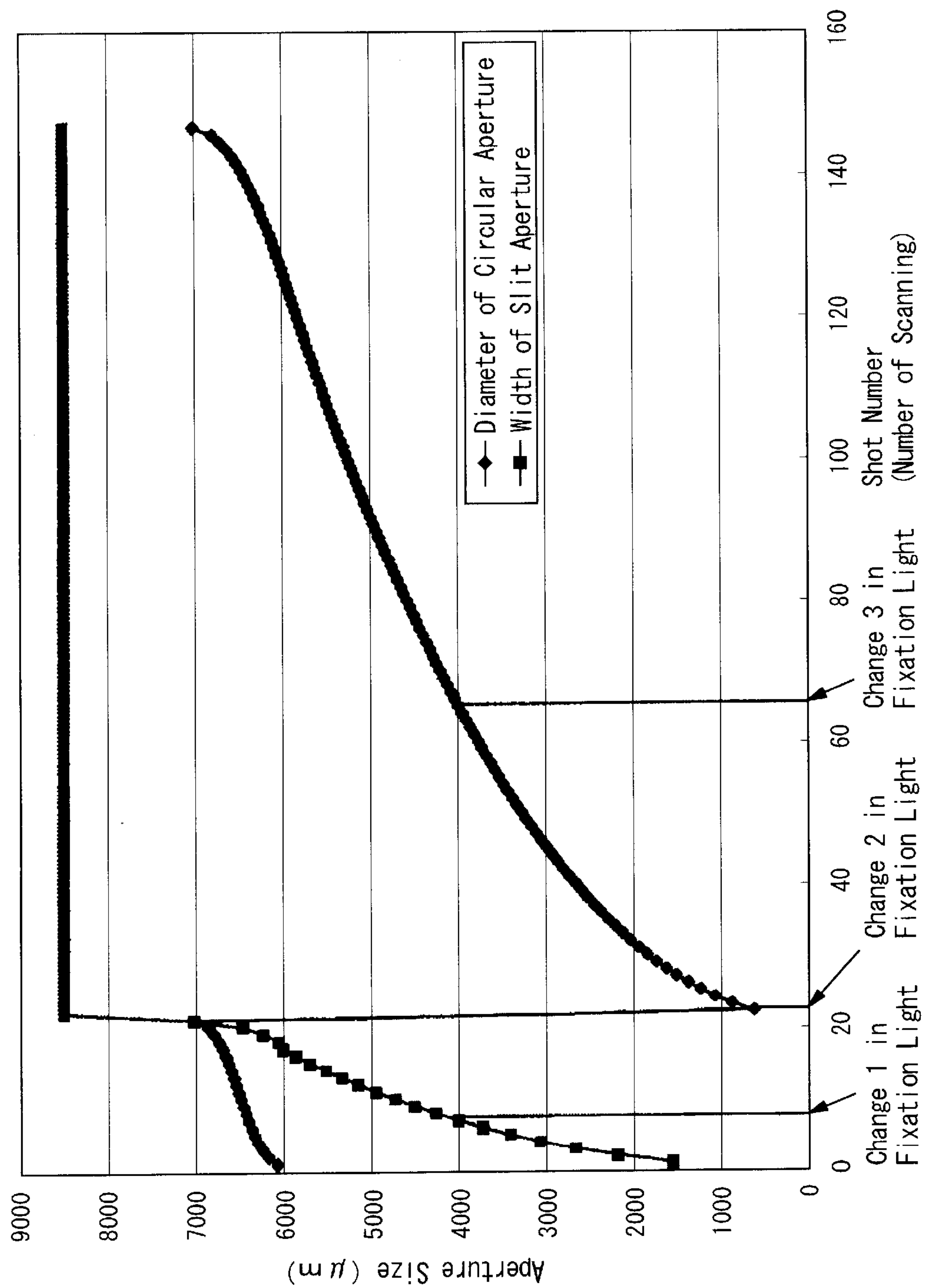
FIG. 3 is a graph showing a driving profile of each aperture corresponding to progress of a keratorefractive surgery.
Figure 4:
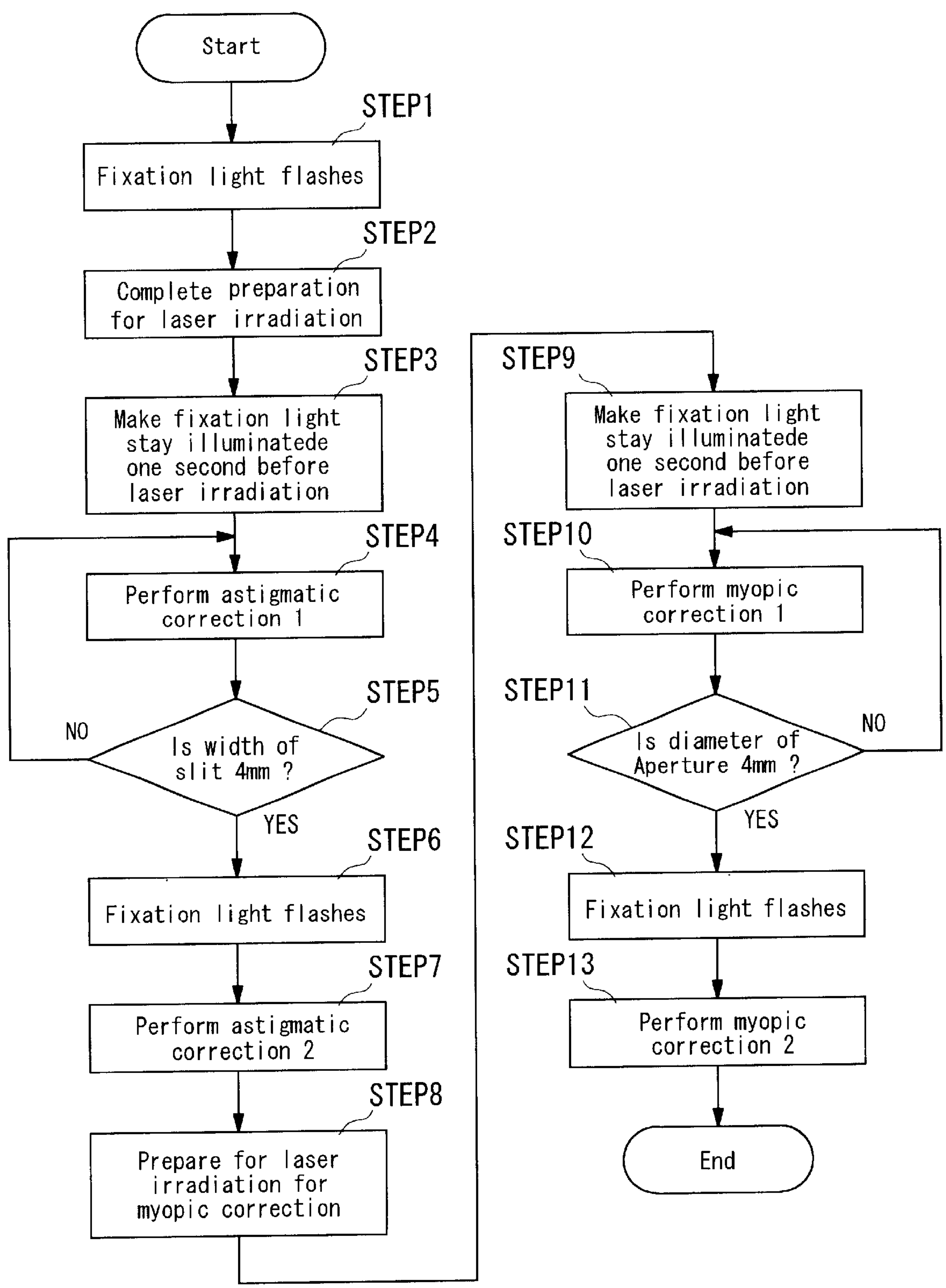
FIG. 4 is a flow chart showing changes in illumination status of a fixation light during the keratorefractive surgery.

FIG. 3 is a graph showing a driving profile of each aperture corresponding to progress of a keratorefractive surgery, and FIG. 4 is a flow chart showing changes in illumination status of the fixation light 20 during the keratorefractive surgery. In FIG. 3, the horizontal axis shows the number of scanning the laser beam, and the vertical axis shows the size of the opening region of the apertures. In this graph, ♦ indicates the circular aperture 15, and ■ indicates the slit aperture 16. For astigmatic correction, it is arranged that the direction of the opening of the slit aperture 16 should be preset by the driving device 45 so that the width of the slit opening should change in the direction of the steepest meridian of astigmatism.

The size of the opening region of the circular aperture 15 is extended so as to fit an optical zone (a region to be optically corrected) from the beginning. Further, the region is gradually extended to form a transition zone. The opening width of the slit aperture 16 is narrow at first (0.6 mm or so), and it is gradually extended to form the optical zone and the transition zone. The sizes of the optical zone and the transition zone are predetermined as a condition for the surgical operation (in the present embodiment, they are 3 mm and 3.5 mm from the center of the optical zone, respectively.) The laser irradiation for astigmatic correction is carried out in accordance with an ablation program for astigmatic correction inputted by using the computer 9. The control unit 40 changes the fixation light 20 to flashing by controlling the light control unit 46. At this point, the operator instructs the patient to fix his/her eye E on the fixation light 20. Then, when the illumination status of the fixation light 20 is changed from flashing to staying illuminated, the operator further instructs the patient to fix the eye E on the light 20 with more attention (STEP 1).

After confirming the patient's eye fixation on the fixation light 20, while the operator performs more accurate alignment of the eye E by using the controller 6, he/she prepares for carrying out the laser irradiation at any moment (STEP 2). Then, the operator manipulates the foot switch 8 to give the control unit 40 a signal for commencing the laser irradiation. When the foot switch 8 is operated, the control unit 40 changes the fixation light 20 to staying illuminated by controlling the light control unit 46. Then, the laser irradiation is commenced in one second after the change in illumination status occurs (STEP 3).

The moving direction of the laser beam is changed by driving the mirror 13 and the image rotator 14, and then the region limited by the slit aperture 16 is approximately evenly ablated. This process provides one scan (for onefourth of a second or so). Then, while changing the opening width of the slit aperture 16, the operator repeats this process to carry out ablation for flattening the cornea Ec in the direction of the steepest meridian (STEP 4).

When the width of the image of the opening region of the slit aperture 16 on the cornea Ec reaches 4 mm, the control unit 40 changes the fixation light 20 to flashing by controlling the light control unit 46 (STEP 5, STEP 6, and Change 1 in the fixation light in FIG. 3). It should be noted that the width of the image of the opening region of the slit aperture 16 on the cornea Ec may be detected in accordance with the opening width of the slit aperture 16 inputted by using the ablation program of the computer 9.

A period when the optical zone is ablated in width (diameter) of 3 to 4 mm from the starting point is extremely important to maintain and improve the patient's eyesight because the region to be ablated during this period is the central part of the eye E. Accordingly, the operator should encourage the patient to properly fix his/her eye on the fixation light 20 during this period. The fixation light 20 should stay illuminated for this period, and it is made to flash after this period as described above. In such a manner, the patient can recognize that the surgical operation comes to the step in which a deviation of the eye E from the fixation light 20 produces relatively small effect, and he/she can be relaxed while keeping the eye E fixed on the fixation light 20.

Subsequent to that, laser irradiation is carried out based on the ablation program. When the width of the image of the opening region of the slit aperture 16 is beyond 6 mm, the movement of the opening of the slit aperture 16 is changed so as to form the transition zone smoothly connecting the optical zone and a non-ablation zone. The control unit 40 gradually extends the opening region of the circular aperture 15 in accordance with the ablation program of the computer 9 for the transition zone while extending the opening width of the slit aperture 16. At the same time, the control unit 40 carries out laser irradiation for the transition zone which is larger than the optical zone (STEP 7). The size of the transition zone has been also predetermined from the beginning as a condition for the surgical operation.

In the present embodiment, the fixation light 20 is made to flash when the width of the image of the opening region of the slit aperture 16 on the cornea Ec reaches 4 mm, but the procedure should not be limited to this manner. In order to minimize the burden on the patient, for ablating the optical zone, it may be required to predetermine the period which is important for maintaining and improving the patient's eyesight and the period which is relatively not important compared to the former period in terms of the patient's eye fixation necessary during ablation in consideration of total operation time.

Myopic Correction

Once the laser irradiation for astigmatic correction is completed, laser irradiation for myopic correction is then subsequently carried out. When myopic correction is carried out, the opening width of the slit aperture 16 is extended to the position where there is no effect on laser irradiation. Further, the opening diameter of the circular aperture 15 having been extended for astigmatic correction is once narrowed to an opening diameter based on data for myopic correction. The time period of preparation for laser irradiation (changing the diameter of each aperture, and so on) lasts for a few seconds (STEP 8). After completing the preparation for irradiation, just one second before the laser irradiation for myopic correction, the control unit 40 changes the fixation light 20 to staying illuminated by controlling the light control unit 46 (STEP 9 and Change 2 in the fixation light in FIG. 3). In such a manner, the patient can understand that he/she should not deviate the eye E from the fixation light 20, and the patient may keep the eye E fixed on the light 20 with great attention while the light 20 stays illuminated.

In the present embodiment, the fixation light 20 is made to stay illuminated one second before carrying out laser irradiation, but the procedure should not be limited to this manner. The change in the fixation light 20 may be made shortly before commencement of laser irradiation so that the patient can calmly fix the eye E when laser irradiation is commenced.

Thereafter, an irradiation region for myopic correction for the first laser irradiation is determined by the narrowed opening diameter of the circular aperture 15, and the laser beam is moved by sequentially moving the mirror 13 in the same manner for carrying out the laser irradiation as described above. Then, every time the laser beam completes one scan, the rotation of the image rotator 14 changes the moving direction of the laser beam so that the region limited by the circular aperture 15 can be evenly ablated. This procedure is repeated for myopic correction every time the opening region of the circular aperture 15 is sequentially changed (extended) in size (STEP 10).

When the diameter of the image of the opening region of the circular aperture 15 on the cornea Ec reaches 4 mm, the control unit 40 changes the fixation light 20 to flashing by controlling the light control unit 46 (STEP 11, STEP 12, and Change 3 in the fixation light in FIG. 3). Because of this change in illumination status of the fixation light 20, the patient can recognize that the surgical operation comes to the step in which a deviation of the eye E from the fixation light 20 produces relatively small effect, and he/she can be relieved while keeping the eye E fixed on the fixation light 20. After that, the laser irradiation is repeatedly carried out in the same way as described above until the diameter of the image of the opening region of the circular aperture 15 reaches 6 mm. Subsequently, ablation in the optical zone and transition zone is performed (STEP 13).

In the present embodiment, 147 scans are carried out until astigmatic correction and myopic correction are completed. Among those scans, the 22nd through 147th scans are performed for myopic correction which takes 30 seconds or so. The change in illumination status of the fixation light 20 is made to occur at the stage of the 66th scan (Change 3 in the fixation light in FIG. 3), and the patient is required to fix the eye E on the light 20 for about 10 seconds with greater attention until the fixation light is changed in illumination status. A psychological stress is greatly minimized compared with the conventional procedure. Furthermore, in the present embodiment, the changes in illumination status of the fixation light 20 from staying illuminated to flashing inform the patient of the changes in the irradiation regions of the laser beam. However, the procedure should not be limited to this manner. For example, a change in color (from red to yellow and the like) or in light intensity of the fixation light 20 may notify the patient about the changes. Also, another light source may be provided for changing a color or light intensity of a background of the fixation light 20, which makes a change in the illumination status around the fixation light 20, whereby the patient is informed without any changes in the light 20 itself.

Figure 5:
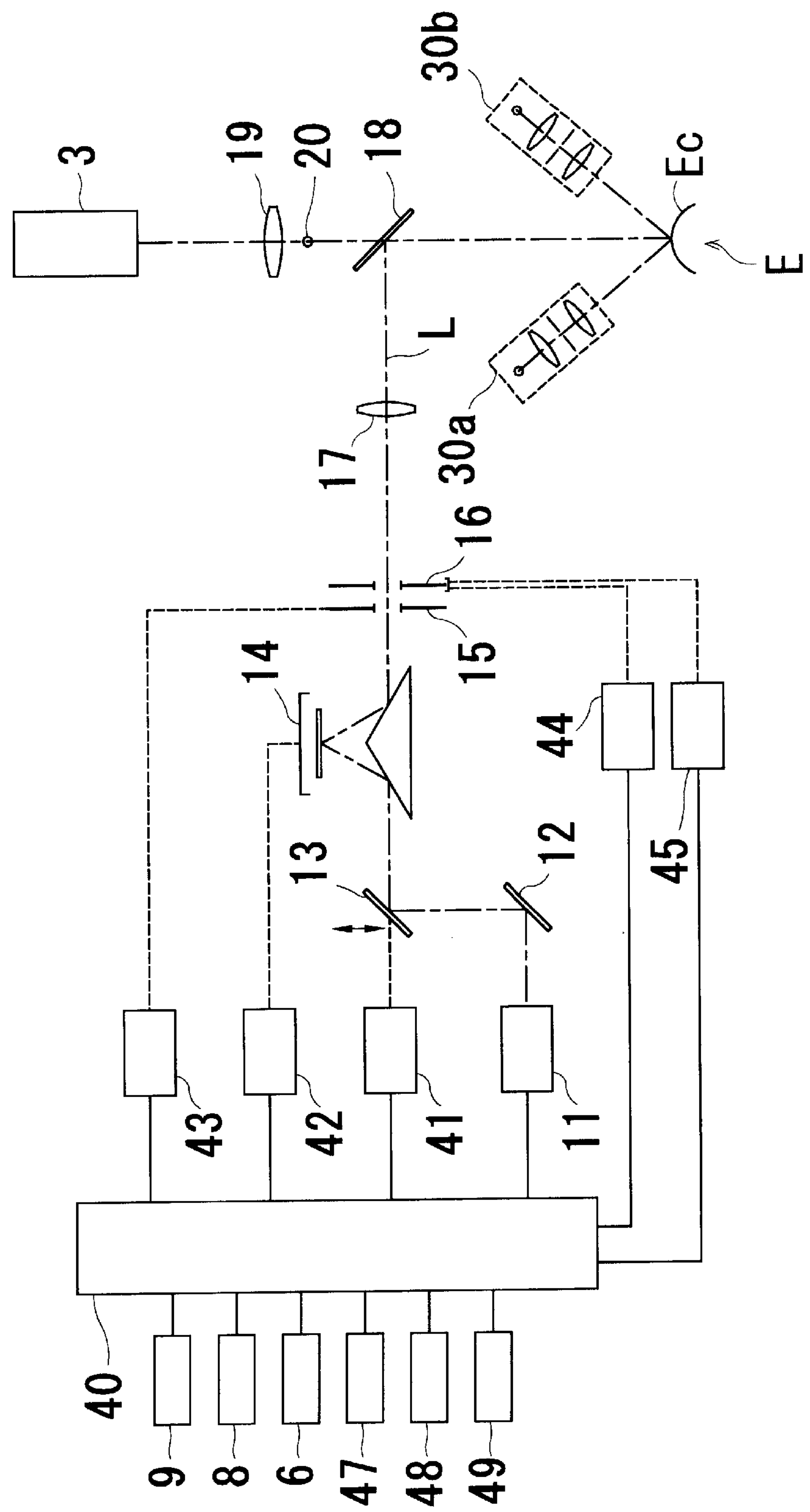
FIG. 5 is a schematic configuration of an optical system and a control system of the apparatus consistent with a modified embodiment.

Furthermore, the patient may be informed by another method which does not change the illumination status of the fixation light 20. As illustrated in FIG. 5, a vibrator 47, which vibrates corresponding to a signal from the control unit 40, may be attached to the patient (for example, having the patient hold the vibrator 47). Instead of the changes in illumination status of the fixation light 20, the vibrations of the vibrator 47 can inform the patient when the specified irradiation regions are changed.

Moreover, as illustrated in FIG. 5, display means 48 constituted of an LED and the like may be disposed at a position on the main body 1 where the operator can easily observe. Accordingly, not only the patient but also the operator can obtain the information about the changes of the specified irradiation regions. With this arrangement, a change in the status of the display means 48 (for instance, a change in illumination status of the LED from staying illuminated to flashing or from flashing to staying illuminated) coincides with a change in the status of an informing means (a fixation light, a vibrator, and the like) for informing the patient, whereby the operator is capable of recognizing the changes of the irradiation regions and encouraging the patient in careful eye fixation by talking to him/her. Also, a sound generator may be employed, whereby differences in intensity or pitch of a sound can inform the patient. In this case, both the operator and the patient can be informed by a single informing means.

In addition, a voice generating means 49 constituted of a speaker and the like may be provided in the main body 1, whereby the operator's countdown during the important period for maintaining and improving the patient's eyesight (in the present embodiment, during the period when the fixation light stays illuminated) can make the patient psychologically relieved.

Also, the aperture is used to change the laser irradiation regions in the description presented above, but the present invention can be applied to a keratorefractive surgery apparatus of which a spot laser beam 1 to 3 mm or so in diameter scans to ablate the cornea Ec with a galvano-mirror and the like.

Moreover, the application of the present invention is not limited to corneal surgery apparatuses, and it can be employed for any laser surgery apparatus used for an surgical operation in which eye fixation of a patient is required. For example, as for a photocoagulator employed for treating a fundus, illumination status of a fixation light may be changed according to the case in which photocoagulation is carried out near a central fovea and to the case in which photocoagulation is carried out at such a position where laser irradiation can be performed more than ten times in a single step. In this configuration, a shift switch and the like which change the illumination status of the fixation light should be provided in the main body of the apparatus. After changing the illumination status of the fixation light with the switch, the operator changes irradiation regions with a manipulator, a joystick, and the like to perform photocoagulation.

As described above, according to the present invention, a patient can release excessive tension by informing him/her of a degree of importance of keeping his/her eye fixed when a patient's eye fixation is constantly required. Accordingly, it can be expected that the patient's fatigue will be minimized, and a good result of a surgical operation will be obtained.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser surgery apparatus for performing surgery on a patient's eye by irradiating a laser beam thereonto comprising:

irradiation means provided with an irradiation optical system for irradiating the laser beam onto the patient's eye;

eye fixation target presenting means for presenting an eye fixation target for the patient's eye fixation;

computing means for computing control data based on data on conditions for a surgical operation and for dividing an operation period into a first period and a second period, the first period during which the patient's eye fixation is important and the second period during which the patient's eye fixation is relatively not important compared to the first period;

control means for controlling the irradiation means based on the computed control data; and informing means for informing the patient of at least either that an operation step is in the first period or that the operation step is in the second period or both.

2. The laser surgery apparatus according to claim 1, wherein the informing means informs by changing status of presentation of the fixation target presented by the eye fixation target presenting means.

3. The laser surgery apparatus according to claim 2, wherein the informing means informs that the operation step is in the first period by making the fixation target stay illuminated and that the operation step is in the second period by making the fixation target flash.

4. The laser surgery apparatus according to claim 2, wherein the informing means informs by changing at least either a color or light intensity of the fixation target or both.

5. The laser surgery apparatus according to claim 1, further comprising second informing means for informing an operator simultaneously with the informing means.

6. The laser surgery apparatus according to claim 1, wherein the informing means includes means for informing the patient of a remaining time of at least either the first period or the second period or both.

7. The laser surgery apparatus according to claim 1, wherein the control means carries out the laser irradiation by controlling the irradiation means in accordance with information provided by the informing means.

8. The laser surgery apparatus according to claim 1, wherein the irradiation means comprises:

a laser light source emitting an excimer laser beam;

an aperture, disposed in the irradiation optical system, of which an opening region is changeable; and a projecting lens, disposed in the irradiation optical system, for projecting the aperture onto a cornea of the patient's eye, and wherein the informing means informs in accordance with a change of the opening region of the aperture.

9. The laser surgery apparatus according to claim 1, further comprising input means for inputting data on a refractive correction as the data on conditions for a surgical operation, wherein the irradiation means comprises:

a laser light source emitting an excimer laser beam for ablating a cornea of the patient's eye; and changing means, disposed in the irradiation optical system, for changing a zone to be ablated with the laser beam, the computing means obtains the control data on the laser light source and the changing means in accordance with the inputted data on refractive correction, and the informing means informs that the operation step is in the first period in which a refractive power within a specific region including a corneal apex is changed.

10. A laser surgery apparatus for performing surgery on a patient's eye by irradiating a laser beam thereonto comprising:

irradiation means provided with an irradiation optical system for irradiating the laser beam onto the patient's eye;

control means for controlling the irradiation means; and informing means including a vibrator giving the patient a vibration for informing the patient of at least either a first period of a laser irradiation period or a second period of the laser irradiation period or both.

11. A laser surgery apparatus for correcting a refractive error of a patient's eye by ablating its corneal tissue with a laser beam comprising:

an ablation unit which includes a laser light source emitting the laser beam and an irradiation optical system provided with an aperture of which an opening region is changeable and with a projecting lens which projects the aperture on a cornea of the patient's eye;

an eye fixation target presenting unit which presents an eye fixation target for the patient's eye fixation;

a computing unit which computes control data based on data on conditions for a surgical operation and divides an operation period into a first period and a second period, the first period during which the patient's eye fixation is important and the second period during which the patient's eye fixation is relatively not important compared to the first period;

an informing unit which informs the patient of at least either that an operation step is in the first period or that the operation step is in the second period or both; and a control unit which controls the informing unit in accordance with a change of the opening region of the aperture based on the computed control data.

12. The laser surgery apparatus according to claim 11, wherein the informing unit includes the eye fixation target presenting unit, and the control unit changes status of presentation of the fixation target by controlling the eye fixation target presenting unit.

13. The laser surgery apparatus according to claim 12, wherein the informing unit informs that the operation step is in the first period by making the fixation target stay illuminated and that the operation step is in the second period by making the fixation target flash.

14. A laser surgery apparatus for operating on a patient's eye by irradiating a laser beam thereonto comprising:

an irradiation unit which includes a laser light source emitting the laser beam and an irradiation optical system for irradiating the emitted laser beam onto the patient's eye;

an eye fixation target presenting unit which presents a fixation target for the patient's eye fixation;

a computing unit which computes control data based on data on conditions for a surgical operation and divides an operation period into a first period and a second period, the first period during which the patient's eye fixation is important and the second period during which the patient's eye fixation is relatively not important compared to the first period; and a control unit which controls the eye fixation target presenting unit to inform the patient of at least either that an operation step is in the first period or that the operation step is in the second period or both by changing status of presentation of the fixation target.

15. The laser surgery apparatus according to claim 14, wherein the eye fixation target presenting unit is controlled by the control unit so as to change at least any one of illumination status, color, and light intensity of the fixation target.

16. The laser surgery apparatus according to claim 14, wherein the control unit controls the eye fixation target presenting unit to inform that the operation step is in the first period by making the fixation target stay illuminated and that the operation step is in the second period by making the fixation target flash.

* * * * *